United States Patent
Gray et al.

(10) Patent No.: US 11,304,730 B2
(45) Date of Patent: Apr. 19, 2022

(54) TETHERED RESTRAINT OF VERTEBRAL BODIES

(71) Applicant: OrthoPediatrics Corp., Warsaw, IN (US)

(72) Inventors: Angus James Gray, New South Wales (AU); Evangelos Tozakoglou, Fort Wayne, IN (US); Matt Prygoski, Warsaw, IN (US); Collin Gibbs, Columbia City, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 2 days.

(21) Appl. No.: 16/228,973

(22) Filed: Dec. 21, 2018

(65) Prior Publication Data
US 2019/0192190 A1    Jun. 27, 2019

Related U.S. Application Data

(60) Provisional application No. 62/609,787, filed on Dec. 22, 2017.

(51) Int. Cl.
*A61B 17/70* (2006.01)
*A61B 17/80* (2006.01)
*A61B 17/86* (2006.01)

(52) U.S. Cl.
CPC ...... *A61B 17/7005* (2013.01); *A61B 17/7001* (2013.01); *A61B 17/7007* (2013.01); *A61B 17/7032* (2013.01); *A61B 17/809* (2013.01); *A61B 17/8625* (2013.01)

(58) Field of Classification Search
CPC ............ A61B 17/7001; A61B 17/7022; A61B 17/7019; A61B 17/7031
See application file for complete search history.

(56) References Cited

U.S. PATENT DOCUMENTS

| | | | |
|---|---|---|---|
| 5,129,388 A | 7/1992 | Vignaud et al. |
| 5,147,360 A | 9/1992 | Dubousset |
| 5,154,719 A | 10/1992 | Cotrel |
| 5,584,835 A | 12/1996 | Greenfield |
| 6,077,262 A | 6/2000 | Schlapfer et al. |
| 6,149,653 A | 11/2000 | Deslauriers |
| 6,221,107 B1 | 4/2001 | Steiner et al. |
| 7,090,690 B2 | 8/2006 | Foerster et al. |
| D601,702 S | 10/2009 | Gotfried |
| 7,909,826 B2 | 3/2011 | Serhan et al. |
| D642,270 S | 7/2011 | McAfee |
| 8,123,749 B2 | 2/2012 | Serhan et al. |
| 8,133,258 B2 | 2/2012 | Serhan et al. |

(Continued)

FOREIGN PATENT DOCUMENTS

| | | |
|---|---|---|
| AU | 2008262019 | 12/2008 |
| AU | 2010229850 | 9/2010 |

(Continued)

*Primary Examiner* — Ellen C Hammond
(74) *Attorney, Agent, or Firm* — Gerald W. Roberts; John V. Daniluck; Dentons Bingham Greenebaum LLP

(57) ABSTRACT

Methods and devices for the tailored restraint of two separate bones, in which the bones are generally permitted to rotate relative to one another, or move toward each other, but are restrained from separating beyond a predetermined, fixed distance. In some embodiments, the restraint is provided by compressing a tether into a notched groove.

7 Claims, 12 Drawing Sheets

(56) References Cited

U.S. PATENT DOCUMENTS

| | | |
|---|---|---|
| 8,273,086 B2 | 9/2012 | Serhan et al. |
| 8,403,958 B2 * | 3/2013 | Schwab .............. A61B 17/7022 606/246 |
| 8,888,818 B2 | 11/2014 | Serhan et al. |
| D746,461 S | 12/2015 | Butler et al. |
| 9,492,165 B2 | 11/2016 | Serhan et al. |
| 9,681,894 B2 | 6/2017 | Nichols et al. |
| 9,855,033 B2 | 1/2018 | Bennett et al. |
| 2006/0271105 A1 | 11/2006 | Foerster et al. |
| 2009/0030466 A1 | 1/2009 | Strauss |
| 2009/0254125 A1 | 10/2009 | Predick |
| 2012/0029567 A1 | 2/2012 | Zolotov |
| 2015/0289986 A1 | 10/2015 | Lee et al. |
| 2017/0027616 A1 | 2/2017 | Serhan et al. |

FOREIGN PATENT DOCUMENTS

| | | |
|---|---|---|
| EP | 2335603 | 6/2011 |
| WO | 2006037131 | 4/2006 |
| WO | 2008011417 | 1/2008 |
| WO | 2009042951 | 4/2009 |
| WO | 2013190431 | 12/2013 |

* cited by examiner

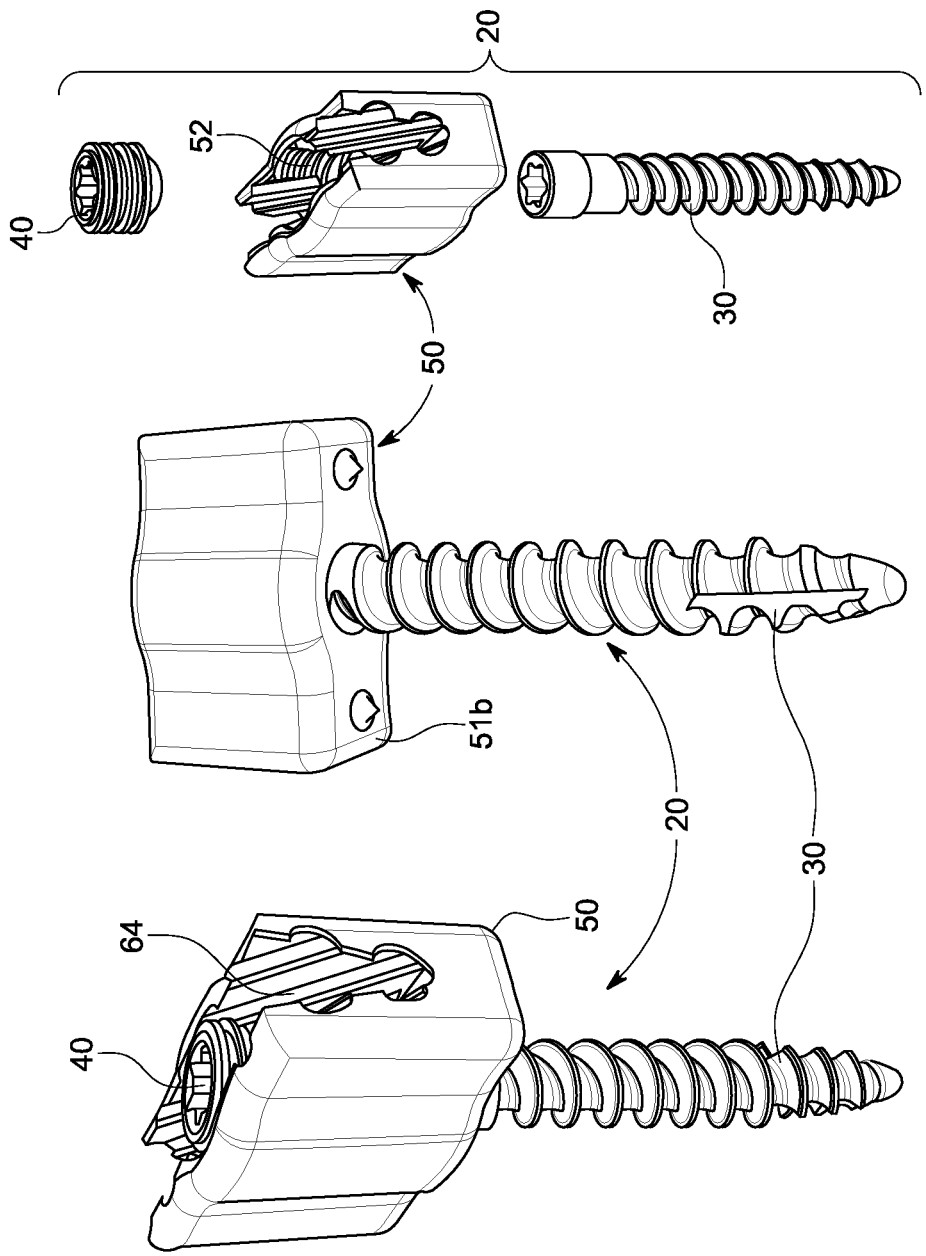

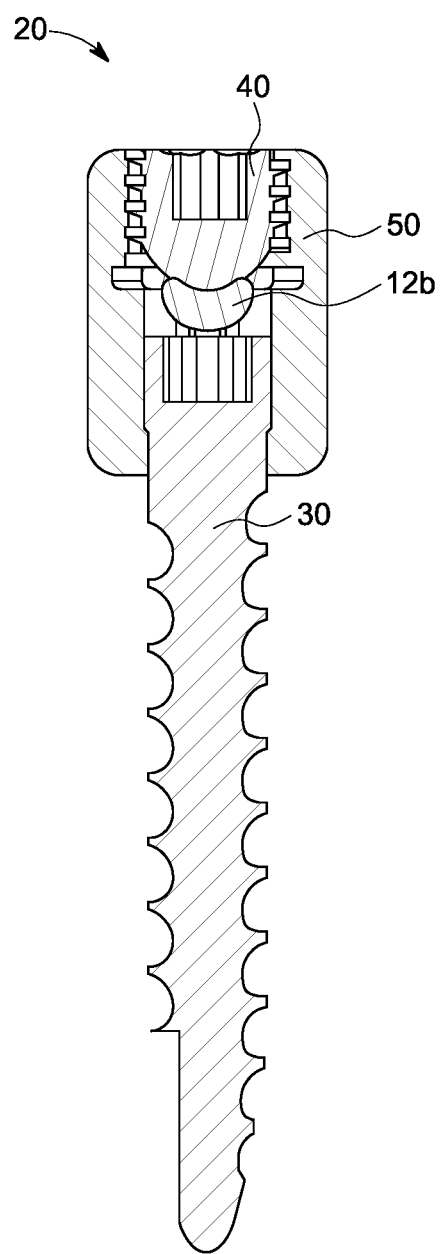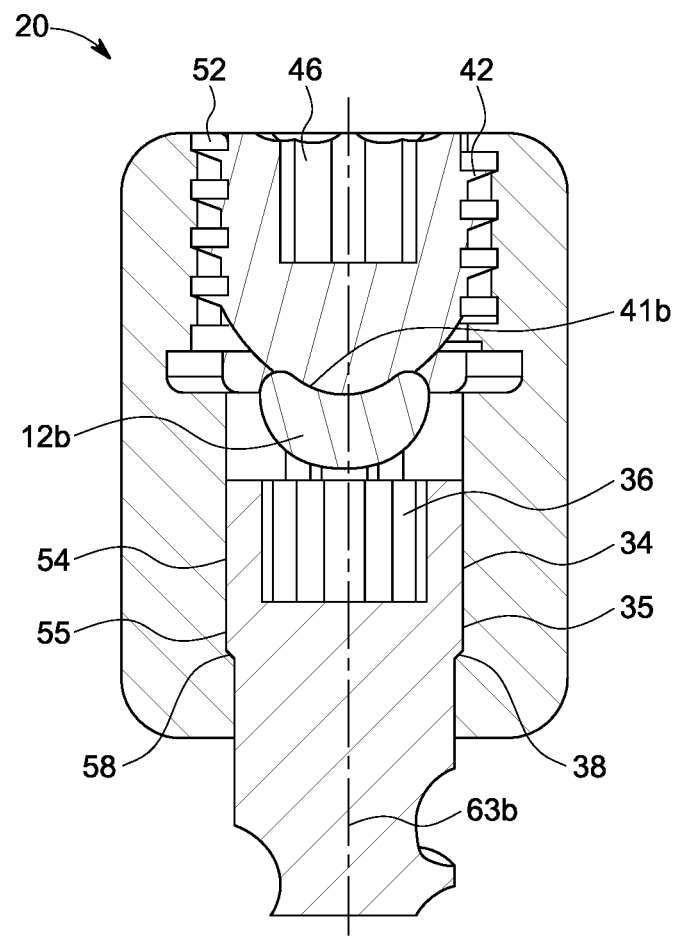
FIG. 15
FIG. 16

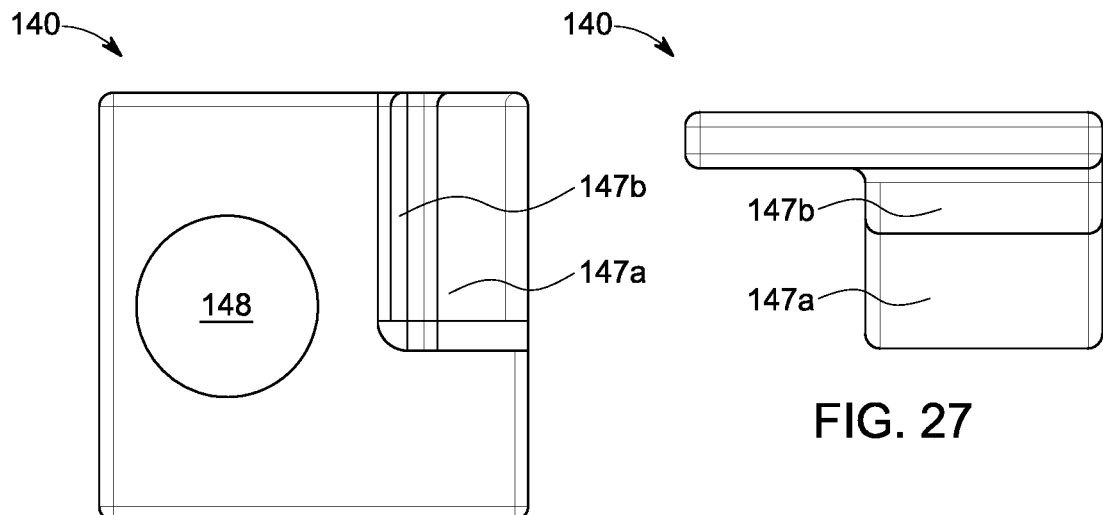
FIG. 26
FIG. 27
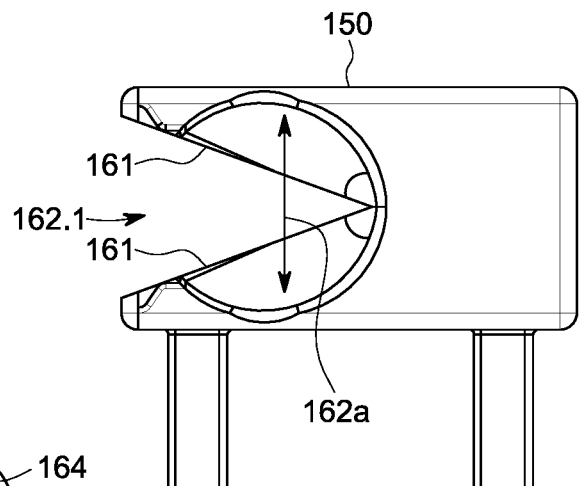
FIG. 28
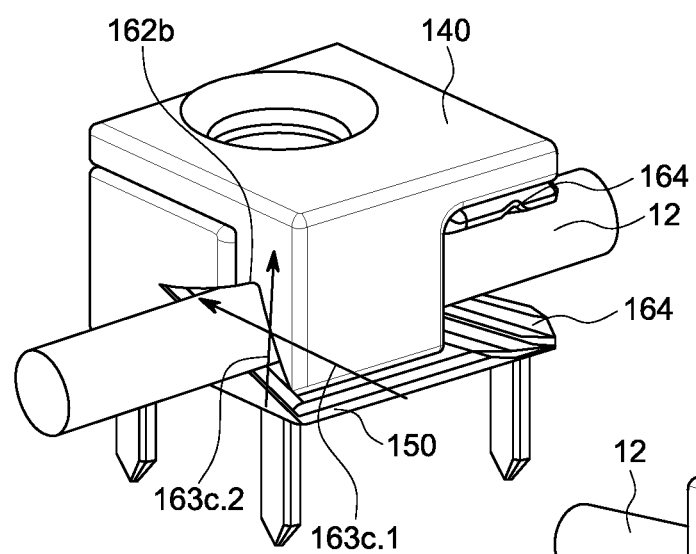
FIG. 29
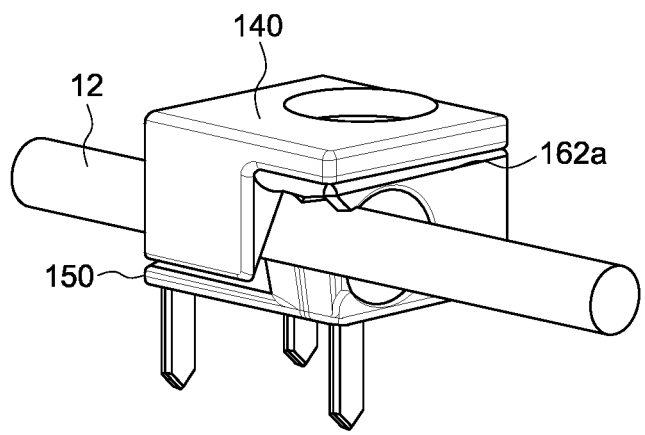
FIG. 30

TETHERED RESTRAINT OF VERTEBRAL BODIES

CROSS REFERENCE TO RELATED APPLICATION

This application claims the benefit of priority to U.S. Provisional Patent Application Ser. No. 62/609,787, filed Dec. 22, 2017, incorporated herein by reference.

FIELD OF THE INVENTION

Various embodiments of the present invention pertain to apparatus and methods for securing two objects by a flexible connection, and in yet other embodiments for securing the interconnection of two vertebrae with a tether.

BACKGROUND OF THE INVENTION

Vertebral body tethering (VBT) remains a procedure in the experimental phase. The behavior of long bone physes are well known and the effects of guided growth fairly predictable. This is not the case with the spine. Each vertebra has 2 end plates, acting as growth plates. How they respond to guided growth is not yet predictable. Previous work by Betz with the Nitinol staple and other authors shed some light on the topic. However, questions such as amount of tension, segmental differences in tension (and alteration over time under load) and the long term effects on the discs remain unanswered.

Some current systems are not designed for purpose and have significant limitations. One proposed design that utilizes a clam (or jam) cleat has advantages over a fixed head bicortical screw. Some embodiments of the inventions described herein overcome some of the current limitations in novel and nonobvious ways.

SUMMARY OF THE INVENTION

Various embodiments of the present invention pertain to methods and apparatus for a tailored restraint of two bones relative to each other, preferably in which the bones are permitted to rotate relative to one another with some restrictions as to the degree of rotation, are permitted to move toward one another, but which are largely restrained from moving apart from one another.

Various other embodiments of the present invention pertain to tether restraining members that include an open pathway for a flexible connector such as a tether, means for compressing the flexible connector toward the bottom of the pathway, and a plurality of grooves on opposing surfaces of the pathway that are adapted and configured to increase the compression on the flexible connector as it is pulled in one direction. In still further embodiments the pathway is open to the physician for placement of the tether on a side of the restraining member that is proximal (facing) the physician. In yet other embodiments the open side of the pathway is placed on a lateral side of the tether restraining member.

Yet other embodiments of the present invention pertain to methods and apparatus for restraining the movement of a flexible member within a groove of a device attached to a bone. The movement of the flexible connection is opposed by placing the flexible connection in a channel that converges in a first direction so as to laterally and frictionally compress the flexible connection within the channel, and in which the walls that form the channel have a series of grooves or flutes that are angled so as to move the flexible member into further compression within the channel if the flexible member is moved longitudinally in a predetermined direction.

Still further embodiments of the present invention pertain to a member for restraining the movement of a bone with a flexible connection, such that the member includes a channel between opposing walls, and the channel has an open top so that the flexible connection can be installed in the channel between the walls from this open top. Preferably, the bottom of the channel is closed, yet other embodiments pertain to channels that open at the bottom, but which nonetheless converge from top to bottom so as to trap and restrain a flexible connection placed between the walls. However, yet other embodiments contemplate a tether restraining member in which the top of the channel is not open, such that the channel for the flexible connection is an enclosed pathway extending from an entrance to an exit.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting. Persons of ordinary skill will also recognize that CAD renderings may include lines that pertain to changes in surface geometry, and not necessarily to component features.

FIG. 1 is a perspective CAD surface representation of a tethering assembly according to one embodiment of the present invention.

FIG. 2 is a bottom perspective representation of the apparatus of FIG. 1.

FIG. 3 is an exploded representation of the apparatus of FIG. 1.

FIG. 15 is a cutaway view of the apparatus of FIG. 13, with a tether shown compressed.

FIG. 16 is an enlargement of a portion of the apparatus of FIG. 15.

FIG. 26 is a bottom plan view of a portion of the apparatus of FIG. 22

FIG. 27 is a side elevational view of the apparatus of FIG. 26.

FIG. 28 is a side elevational view of a portion of the apparatus of FIG. 24.

FIG. 29 is a perspective representation of a partial assembly (shown without fastener) of the apparatus of FIG. 20, showing a tether in restraint.

FIG. 30 is a perspective view of the apparatus of FIG. 29, from a different perspective.

ELEMENT NUMBERING

Figure 4:
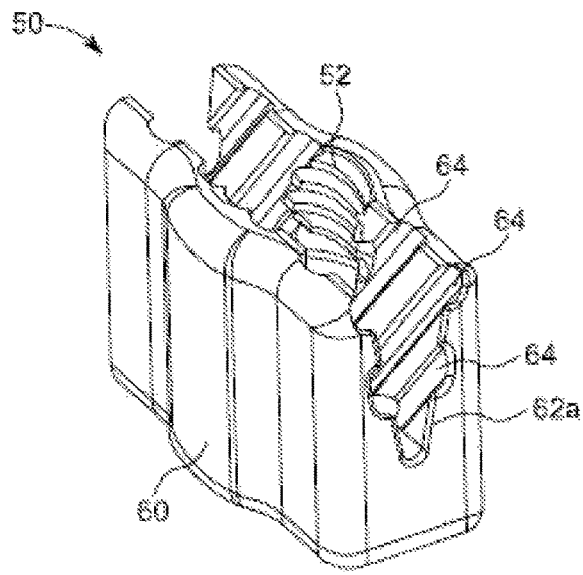
FIG. 4 is a side, top, perspective CAD surface representation of a tether restraining member of FIG. 1 according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| | |
|---|---|
| 10 | vertebrae |
| 12 | tether |
| a | free shape |
| b | compressed shape |
| 20 | tethering assembly |
| 30 | bone fastener |
| 31a | proximal end |
| 31b | distal end |
| 32 | threaded shaft |
| 34 | head |
| 35 | outer diameter |
| 36 | driving pocket |
| 38 | exterior shoulder |
| 40 | cap |
| 41a | proximal end |
| 41b | distal end |
| 42 | threads |
| 46 | driving pocket |
| 47a | wedging surface |
| 47b | abutting surfaces |
| 48 | aperture |
| 50 | tether restraining member |
| 51a | proximal end |
| 51b | distal end; bone contacting surface |
| 52 | interior threads |
| 53 | projections |
| 54 | cylindrical pocket |
| 55 | inner diameter |
| 57a | aperture |
| 57b | abutting surfaces |
| 58 | interior shoulder |
| 59a | open top |
| 59b | closed bottom |
| 60 | lateral walls |
| 61 | inner surfaces |
| 62 | channel, narrowing; V-shape |
| 62.1 | first channel, member |
| 62.2 | second channel, member/cap |
| 62a | entrance |
| 62b | exit |
| 63a | longitudinal axis |
| 63b | vertical axis |
| 63c | direction of convergence |
| 63c.1 | $1^{st}$ channel direction of convergence |
| 63c.2 | $2^{nd}$ channel direction of convergence |
| 63c.3 | $3^{rd}$ channel direction of convergence |
| 64 | grooves; flutes |
| 64a | direction of convergence |
| 65 | tether compression region |
| a | length |
| b | width |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

One embodiment of the present invention proposes a jam cleat (or clam) for the tethered fixation of two vertebrae. A clam cleat can provide good grip of a rope or tether without damaging it. It is expected to work well in vivo. This concept of gripping of the tether is similar to designs used in sailing. On some sailboats, jam cleats are used when the ropes or sheets are usually wet, and such cleats don't tend to slip.

Various embodiments of the present invention described herein utilize a bone screw for fixation of a tethering member to the vertebrae. However, yet other embodiments contemplate the use of a plate. If a vertebral body plate is used, rather than a centrally or otherwise placed fixed head screw, it allows the use of 2 screw fixation, parallel to the endplates. This can be a strong construct. The plate will also have a greater surface area for a clam cleat than a screw. Some embodiments utilizing a plate avoid some aspects of surgery in which a screw is used. By a plate not contacting the centre of the vertebral body, there will be no need to ligate the segmental vessels. This will remove a step form the surgery and, more importantly, does not risk compromising spinal cord blood supply. However, yet other embodiments contemplate the use of bone fasteners. If central, diverging screws are used with the plate, then the segmental vessels would need ligation. Central divergent screws may be biomechanically stronger which could override the blood vessel ligation concern.

Various embodiments of the present invention use a bone fastener and a tether restraining member, or a body plate and a tether restraining member to compress and hold the tether in place. Preferably but optionally, either the restraining member or the plate includes a cap to prevent dislocation of the rope within a channel or passageway of the tethering member. In various embodiments, the cap can thread to the restraining tethering member, slide on the restraining member, or "click on" (vertically) on to the cleat. Preferably but optionally, the cap should also provide some compression to the sides of the cleat, in order to make its grip on the rope more secure. It should be easy to apply and remove thoracoscopically. Regarding material, Ti or PEEK are two candidates, although the brittleness of PEEK may be a factor, and various embodiments of the present invention contemplate the use of any biocompatible material. Wear debris is a concern, so moving surfaces are best avoided or limited.

There should be enough distance between the positioning of the bone fasteners or the ends of the plates to allow reasonable intervertebral movement. It is recognized that a plate may leave less rope between each segment than a screw. The loads may be reduced and the range of movement improved by shortening the plate. An alternative is a rotating plate, provided that wear concerns and debris generation are addressed.

It is preferable to try and close the parietal pleura over the implant. Therefore, a low profile construct is desirable.

In some embodiments of the present invention, it is possible to apply tension to the uncompressed diameter of the rope or tether between the screw or plate fixation points. As to the distribution of the tension along the tether, what is best is unknown. In some embodiments the max tension should be at the apex, tapering to the ends of the construct, although other embodiments contemplate any distribution of tension that is biocompatible and successful in the result. Over tensioning is a concern, and may contribute to the over corrections seen in some reports pertaining to conventional designs used in VBT. Unlike instrumented spinal fusions for scoliosis, where maximal correction is aimed for and achieved intraoperatively, VBT is a long term process. It may be that modest tension and patience is best.

Various embodiments of the present invention contemplate different methods as to how to apply tension. In one embodiment, the tension is applied from one fixed end, travelling down, segment by segment with a tensioning gun, locking as one goes. This is reasonable and applicable to a clam cleat, where the rope should be driven into the base of the cleat to be securely held. An alternative method in yet other embodiments is the use of a compressor to draw the tether restraining members together and then set the rope.

As to the method of surgery and surgical access, access is difficult with the lung being problematic as it commonly obscures the spine. One current system uses positive pressure within the chest cavity, along with a double lumen tube to keep the lung deflated and out of the surgical field. In surgical methods using various embodiments of the present invention, an alternative is the above technique to start the procedure, but then use a mini open approach to each level. This method can be facilitated with the use of an expanding retractor, much along the lines of stents used in vascular surgery. An MIS type tube could be passed sequentially at each level, long enough to reach the vertebra. Around it is an expanding cage to clear the lung from the field. In this way, maintaining positive intrathoracic pressure may not be needed. The apparatus and methods described herein may also be compatible with MIS techniques. Still further surgical methods may be facilitated by using tubes, k wires and cannulated screws.

Yet another potential surgical method includes, for example, to apply a plate to T8, including a mini thoracotomy. A dilator is passed and the expanding retractor deployed. With the T8 body on view, paired parallel K wires are passed via a guide and checked on II. The plate is passed over the wires and then the screws inserted. Rechecking is done via II and then the retractor is closed and the process repeated at the next level.

FIGS. 1, 2, and 3 depict various views of an assembly 20 according to one embodiment of the present invention. Assembly 20 includes means for connecting to a bone, such as by way of screw threads, straps, plates, or any other method. As shown in apparatus 20, a threaded bone screw 30 extends from the underside 51*b* of a tethering restraint member 50. A threaded cap 40 (such as a setscrew) is threadably coupled to the restraining member 50. In some embodiments, a plurality of apparatus 20 are used to interconnect vertebrae. Still further embodiments are useful for tethered interconnection of any bones. Yet further embodiments are useful for flexible interconnection between any two devices, in which some relative motion between the devices is permitted, but in which relative motion that places the flexible interconnection in tension is resisted.

As shown in FIGS. 1, 2, and 3, the apparatus 20 includes a V-shaped trench or channel 62 that is oriented in a proximal-distal manner, relative to the bone fixation member 30. However, it is further understood that the orientation of the channel or groove 62 may be horizontal, or perpendicular to the axis of fixation, and generally parallel to the surface of the vertebrae. Still further, it is understood that various embodiments do not include a cap 40, and the tether in such embodiments is securely held in the groove or channel 62 by means of the V-shape, the narrowness of the channel, and/or the grooves located on the opposing faces of the tether restraining member 50.

Figure 6:
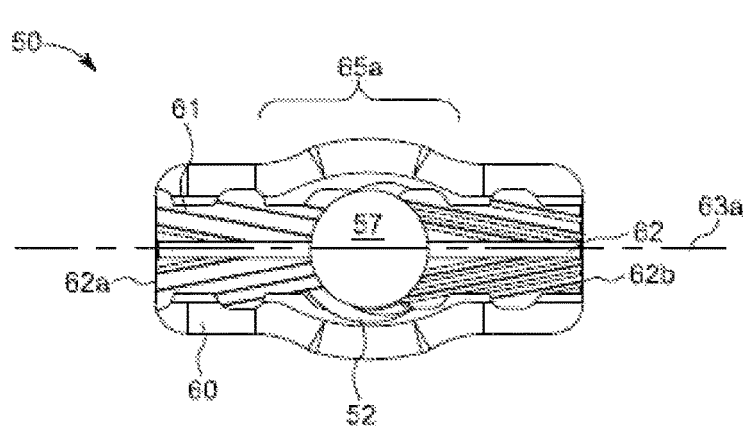
FIG. 6 is a top plan view of the apparatus of FIG. 4.

In one embodiment, channel 62 extends in one vertical direction from an open top 59a to an enclosed bottom, 59b, and in an orthogonal, longitudinal direction from an entrance 62a for a flexible connector to an exit 62b for the flexible connector. Referring to FIGS. 4 and 6, it can be seen that if a flexible connector is placed in the channel from the open top and pulled from the exit 62b, that the grooves or flutes 64 along the channel will tend by friction to move the flexible connector toward the bottom of the channel, as will be further discussed later. In some embodiments, the entrance and exit are on opposite sides of the body 50, such that the pathway of the channel is generally straight. Yet other embodiments of the present invention further contemplate curved pathways, such that the exit and entrance are located on adjacent sides, or for the case where the shape of the body is circular, oval, or rounded, the entrance and exit are spaced apart by less than one hundred eighty degrees.

Figure 7:
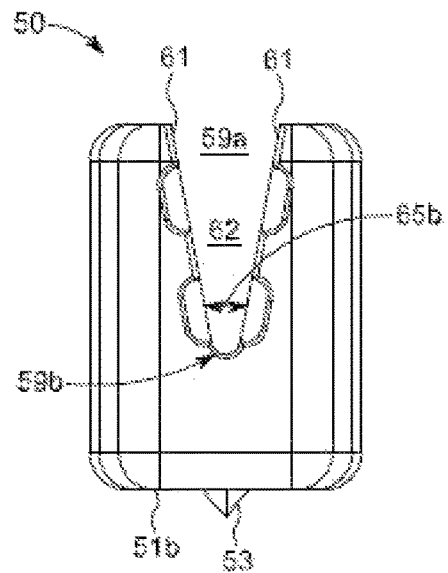
FIG. 7 is an end perspective view of the apparatus of FIG. 4.

FIGS. 4, 5, 6, and 7 depict various views of a tether restraining member 50 according to one embodiment of the present invention. It can be seen that member 50 includes a pair of lateral, opposing walls 60 that preferably extend the entire length of member 50. The opposing inner surfaces 61 in some embodiments are adapted and configured to form a V-shaped groove 62 between the surfaces, as best seen in FIG. 7. However, it is understood that in still other embodiments the opposing inner surfaces 61 are generally parallel, yet can still be adapted and configured to provide compression of a tether as will be described for the V-groove.

The V-groove 62 converges in a direction from the outer (proximal) top of the member 50 toward the bone contacting surface 51b. In yet other embodiments, the V-groove converges in a direction that is generally horizontal relative to the bone contacting surface, and yet further embodiments contemplate any orientation from vertical to horizontal of the V-groove. The included angle of the V is selected to provide a width 65b that is less than the diameter or width of the uncompressed tether.

It is understood that various embodiments of the present invention pertain to the use of flexible tethers placed between adjacent tethering restraint members. The flexible tether may be of any type, including by way of example the use of biocompatible metal or organic materials, exemplary configurations of which include wire, sutures, flat tethers, etc. In some embodiments, the tether material is compressible, and can be squeezed into a channel or groove of the tether restraining member that has a width less than the uncompressed width of the tether. In still other embodiments, such as those using a metal alloy such as titanium or stainless steel, the metal tether does not compress, but is held in place by friction between the walls of a narrowing groove, and in some embodiments with a loading force applied by a cap or set screw.

Therefore, when the tether is placed in this area, it is deformed and placed compressively in a frictional fit as will be seen later. Preferably, this region of tether compression 65 extends along the entire longitudinal length of channel 62. However, as seen in FIG. 6, in some embodiments, the length 65a of this tether compression region occurs only over a portion of the length.

Preferably, at least a portion of this tether compression region 65a occurs underneath the interior threaded receptacle 52, as best seen in FIGS. 4 and 6. In some embodiments, the threaded receptacle 52 is generally centered relative to both the width and the length of the retaining member 50. In yet other embodiments, the restraining member 50 further includes an aperture 57 that is adapted and configured to receive the shaft of a bone screw. As will be seen, the aperture 57 and threaded receptacle 52 are preferably aligned coaxially along a vertical axis 63b (best seen in FIG. 16). Referring to FIG. 6, it can be seen that member 50 has a longitudinal orientation, and in some embodiments includes a longitudinal axis 63a that is preferably a centerline of the V-groove 62. Still further, in some embodiments the member 50 is symmetrical about a plane that extends through longitudinal axis 63a and vertical axis 63b. Although various forms of symmetry and centering have been shown and discussed, it is understood that yet other embodiments include members with little or no symmetry.

As best seen in FIGS. 4 and 6, the channel or V-groove 62 is formed between opposing surfaces 61 of walls 60 that include a plurality of angled grooves or flutes 64. Referring to FIG. 4, it can been seen that there are four (4) grooves or flutes 64 that extend up the inner wall surfaces 61 and reach through the top surface 51. Preferably, these grooves are at an angle between 30 to 60 degrees relative to centerline 63a. However, still further embodiments contemplate grooves of any angle, including for example grooves that are neither nor parallel nor perpendicular to longitudinal axis 63a or vertical axis 63b. Still further, the grooves or flutes 64 shown herein are expressed with a succession of generally flat peaks separated by curving valleys. However, it is understood that the cross sectional shape of the groove or flute can be of any shape, including preferably those shapes that minimize potential damage to the tether or generation of debris, or those shapes that accommodate the frictional restraint of a metal wire.

Figure 13:
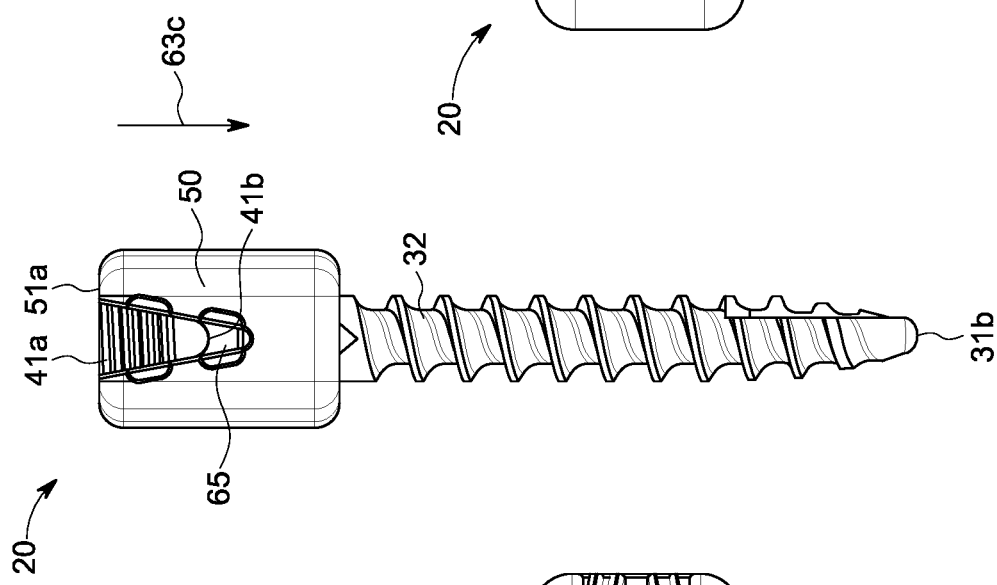
FIG. 13 is a side elevational view of the apparatus of FIG. 1.

Although references made herein to a V-shaped groove, it is understood that the channel, groove, or pathway for the tether within the tethered restraining member is of a shape in which the opposing walls converge toward each other, preferably to a gap between the walls at the bottom of the groove or channel that is not as wide as the uncompressed width of a tether. Referring briefly to FIG. 13, it can be seen that the opposing sidewalls of the tethering restraint member converge toward each other in the direction 63c, which is preferably in a direction toward the bone in which the restraint member is implanted. It is understood that the V-shaped groove contemplates grooves that are U-shaped, Y-shaped, and other converging geometries.

Figure 12:
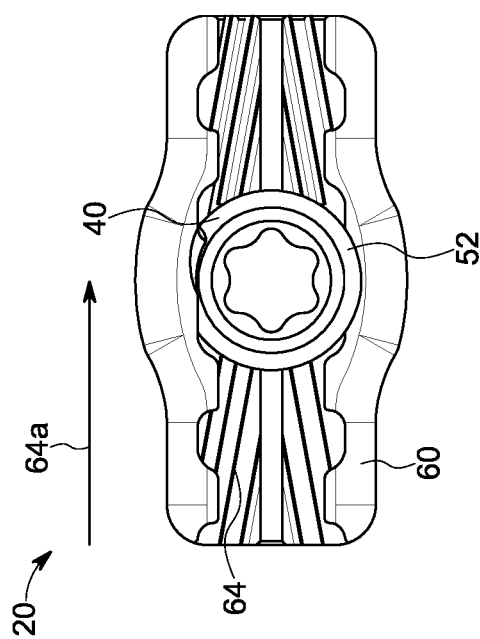
FIG. 12 is a top plan view of the apparatus of FIG. 1

Although grooves 64 are shown extending over the entire inner surfaces 61, it is understood that the grooves in still further embodiments are placed only within the tether compression region 65. Still further, it is appreciated that the grooves 64 are relatively deep and relatively wide spaced. The approximate size of the grooves can be scaled from FIG. 6, in which aperture 57 has a diameter between about two millimeters and three millimeters. However, still further embodiments of the present invention contemplate any shape for size of the groove that is adapted and configured for compressive, frictional grasping of a tether. Referring briefly to FIG. 12, it can be seen that the grooves 64 on opposing sidewalls converge toward each other in direction 64a. However, yet other embodiments of the present invention are not so constrained, and include embodiments in which the grooves 64 on one wall converge toward the bottom of the channel 65 in one lateral direction, but converge in the opposite lateral direction on the opposing wall.

Referring to both FIGS. 12 and 13, it can be understood that if a tether is placed from the open top 59a and directed down toward the closed bottom 59b (both indicated on FIG. 7), that the flexible connector is moving toward increasing amounts of laterally imposed compression and friction between the opposing inner surfaces 61. Referring to FIG. 12, it is understood that if the tether is pulled in the direction 64a of the convergence of the grooves, that pulling in this direction 64a will also act to move the flexible connector in direction 63c, which is toward increasing levels of compression and frictional restraint.

Figure 5:
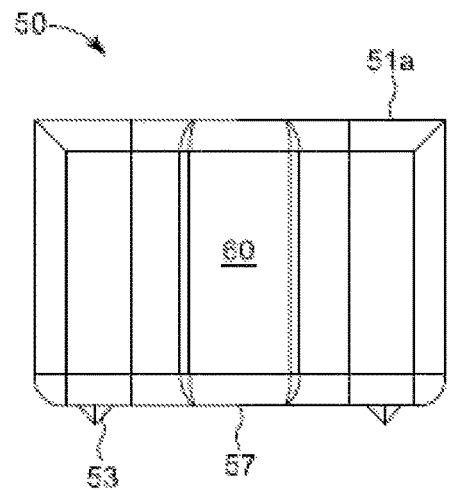
FIG. 5 is a side elevational view of the apparatus of FIG. 4.

Referring to FIGS. 4 and 5, and found in some embodiments but not others, it can be seen that a threaded receptacle 52 is placed centrally within member 50. These grooves receive an optional cap 40 that applies compression to a tether placed within groove or channel 62, although it is understood that in various other embodiments a threaded cap is not required. In some embodiments, as best seen in FIG. 16, the central axis of the threaded receptacle is preferably coaxial with the central axis of aperture 57, which places cap 40 directly above screw 30. However, the present invention also contemplates those embodiments in which the axes of receptacle 52 and aperture 57 are oriented in any manner relative to one another, including for example angular displacements of the two axes and lateral displacements of the two axes. Preferably, the depth of threaded receptacle 52 and the design of cap screw 40 are such that a fully inserted cap screw 40 has a top surface that is generally flush with top surface 51a of member 50.

In some embodiments the undersurface 51b of member 50 is adapted and configured to be in contact with the surface of a bone (or the surface of any tethered device). In such embodiments, there may also be a projection or other slippage-resistant feature 53. It is also understood that in those embodiments in which the V-shape groove 62 is oriented horizontally, that the slippage resistant feature (if it is present) on the exterior of a sidewall 60. In such embodiments, it is recognized that the aperture 57 would likewise be located and extending through that same lateral wall.

Projection 53 in some embodiments provides a structure that penetrates slightly into the bone surface, thus making member 50 less susceptible to slippage or movement once it is placed against the bone surface. However, in still further embodiments, undersurface 51b can include scallops or undercuts to control and manage the contacted surface area of the bone. Further, in yet other embodiments assembly 20 is adapted and configured such that undersurface 51b does not touch the surface of the bone (or tethered device). In such embodiments, the fastening screw 30 is captured on member 50, such as by a locking nut, or in some embodiments the screw is integral with body 50. As also mentioned herein, in yet other embodiments the assembly 20 include plate attachment to the vertebrae in place of a central fastening screw 30.

Figure 9:
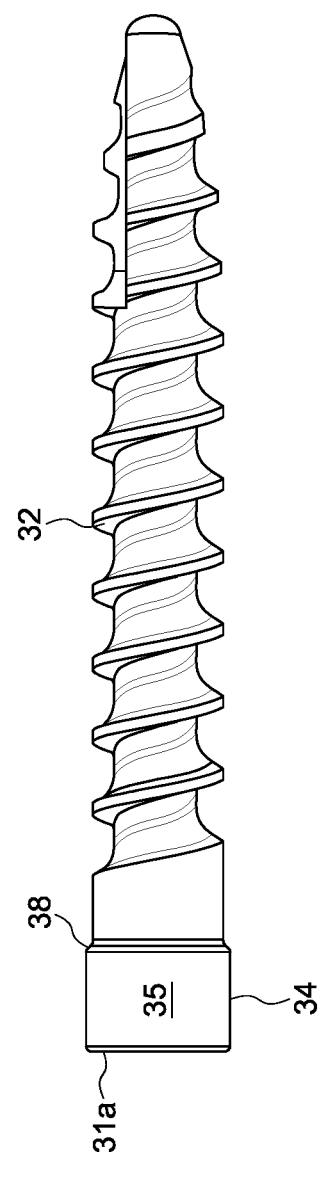
FIG. 9 is a side elevational view of the apparatus of FIG. 8.
Figure 8:
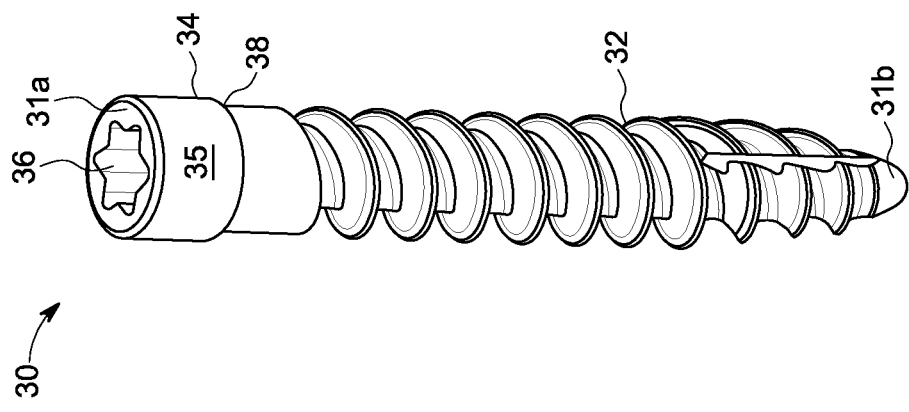
FIG. 8 is a perspective CAD surface representation of a bone fastener according to one embodiment of the present invention, and as shown in FIG. 1.

FIGS. 8 and 9 present different views of a bone fastener 30 according to one embodiment of the present invention. Fastener 30 includes a threaded shaft 32 and a head 34. At the proximal end 31a of screw 30 there is a driving pocket 36 that is adapted and configured to receive therein a tool for applying a torque to fastener 30. At the distal end 31b of fastener 30 is a blunted end, and in some embodiments a vertical undercut that extends through several of the distalmost threads. Cap 34 has a generally cylindrical outer surface 35 that extends from proximal end 31a to an exterior shoulder 36, at which location the outer diameter is reduced.

Figure 11:
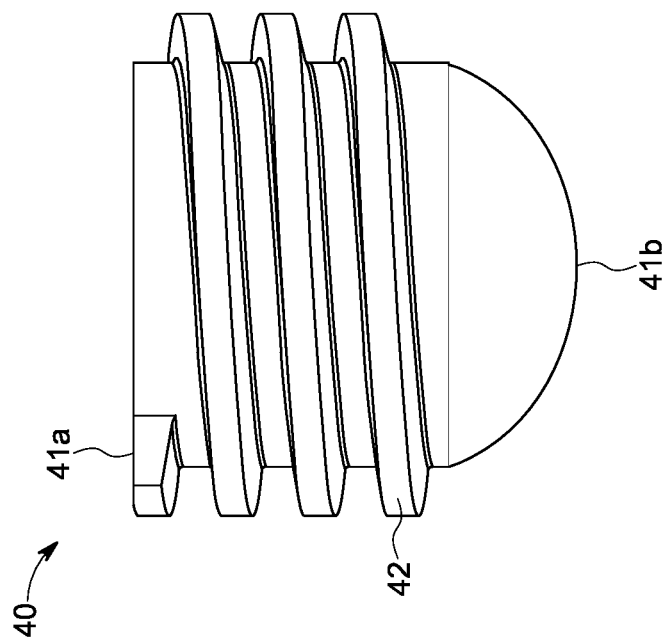
FIG. 11 is a side elevational view of the apparatus of FIG. 10.
Figure 10:
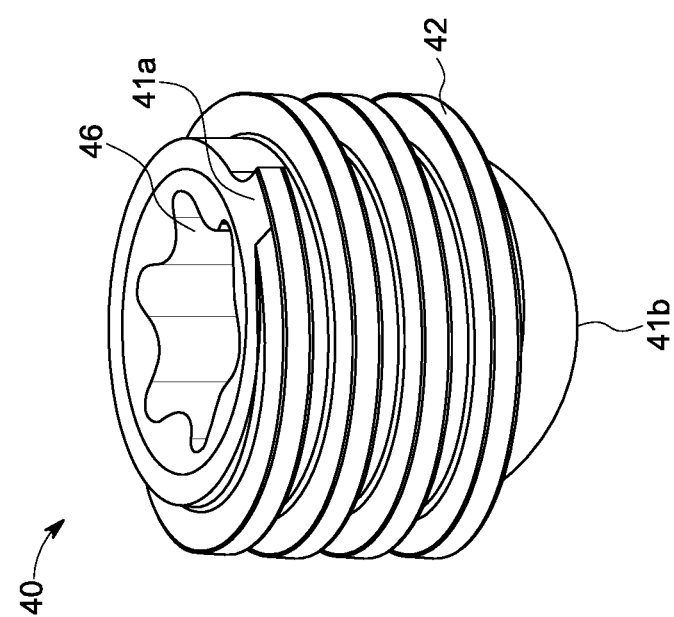
FIG. 10 is a perspective CAD surface representation of a cap of FIG. 1 according to one embodiment of the present invention.

FIGS. 10 and 11 depict two views of an optional threaded cap 40 or set screw that is adapted and configured to be received within the interior threads 52 of tether restraining member 50. The proximal end 41 includes a driving pocket 46 which is preferably adapted and configured to receive the same driving tool used in driving pocket 36 of fastener 30. A plurality of threads 42 extend along a generally cylindrical body of cap 40. The distalmost end 41b of cap 40 is preferably smooth and rounded, and adapted and configured to compress a tether located within channel or groove 62. It is understood that although a smoothly curing underside 41b has been shown and described, various other embodiments contemplate any configuration of underside that will compress the tether 12, preferably without cutting or otherwise damaging the tether material.

Figure 14:
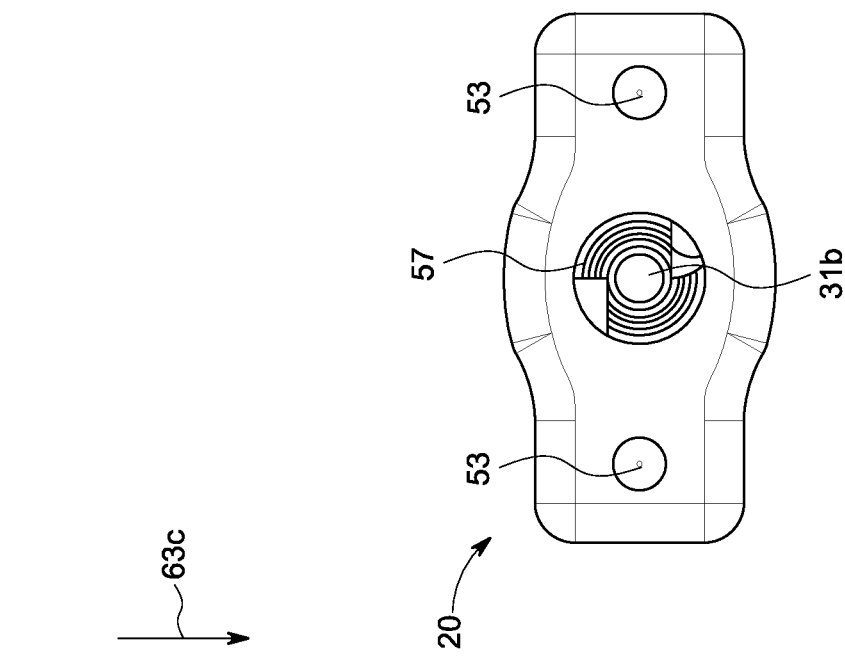
FIG. 14 is a bottom plan view of the apparatus of FIG. 1.

FIGS. 12-14 depict various views of an assembly 20 according to one embodiment of the present invention. A threaded cap 41 has been received within threaded receptacle 52, with the proximal surfaces 41a and 51a being generally flush. A fastener 30 is located within aperture 57 of body 50. FIG. 13 shows an end view of tether compression region 65, as located between inner surfaces 61 of wall 60 and the underside 41b of cap screw 40.

FIGS. 15 and 16 depict cutaway views of assembly 20, and shown with a compressed tether 12b located therein. The tether 12 is placed in a compressed shape 12b that is in contact with under surface 41b (in those embodiments including a cap 40), and further between grooved inner surfaces 61. In the depiction of compressed tether 12b of FIGS. 15 and 16 it is noted that the cross section is taken within the valleys of grooves 64 on opposite sides of the tether. In the groove valleys, the tether material is less compressed than the tether material that is located between the peaks of opposing grooves. Therefore, tether 12 is retained within groove or channel 62 by: (1) compression between peaks; (2) compression between valleys; and (3) the change in the shape of the outer surface of the compressed tether 12b as it extends axially (along axis 63a) from high compression between groove peaks to lesser compression within groove valleys. In this third aspect of tether retention, the segmented "pooching out" of the compressed tether provides additional resistance to slippage of the tether relative to body 50. Thus, in order for a tether 12 to slip once it is captured, not only must the slippage forces overcome frictional forces between groove peaks and frictional forces between groove valleys, the slippage must also overcome the force required to compress the pooched out tether (a compression that is necessary if it is to move from a valley to a peak).

FIG. 16 also shows the manner in which screw 30 is retained within member 50. The outer diameter 35 of fastener head 34 is received in a generally close fit in the inner diameter 55 of cylindrical pocket 54. This close fit, along with the height of head 54 and the depth of pocket 54, to provide stability of the assembled shape and resistance to a rocking motion (i.e., rolling about axis 63a). It is also seen that exterior shoulder 38 of head 34 abuts against interior shoulder 58 of aperture 57. This abutment provides a limit on the distal travel of screw 30 relative to body 50.

It is understood that the retention of fastener 30 within body 50 does not limit the rotation of body 50 relative to fastener 30. However, in those embodiments in which underside 51b includes one or more slippage resistant features 53, that such features will limit the relative rotation. Still further, other embodiments contemplate a locking of head 34 within pocket 54

It is further appreciated from FIGS. 15 and 16 that in some embodiments the underside of the compressed tether 12b preferably does not contact the driving pocket 36 of screw 30. In such embodiments, there is less possibility for the underside of the tether material to be damaged by the surfaces of the pocket. However, in yet other embodiments, the spacing of compression region 65 is adapted and configured such that a portion of the compressed shape 12b does reside within the driving pocket (or other feature) of the bone screw. Still further, in some embodiments it is contemplated to adapt and configure the pocket 36 for less possibility of damage to a compressed tether, with features such as gently rounded shoulders or gently contouring pocket shapes.

Figure 17:
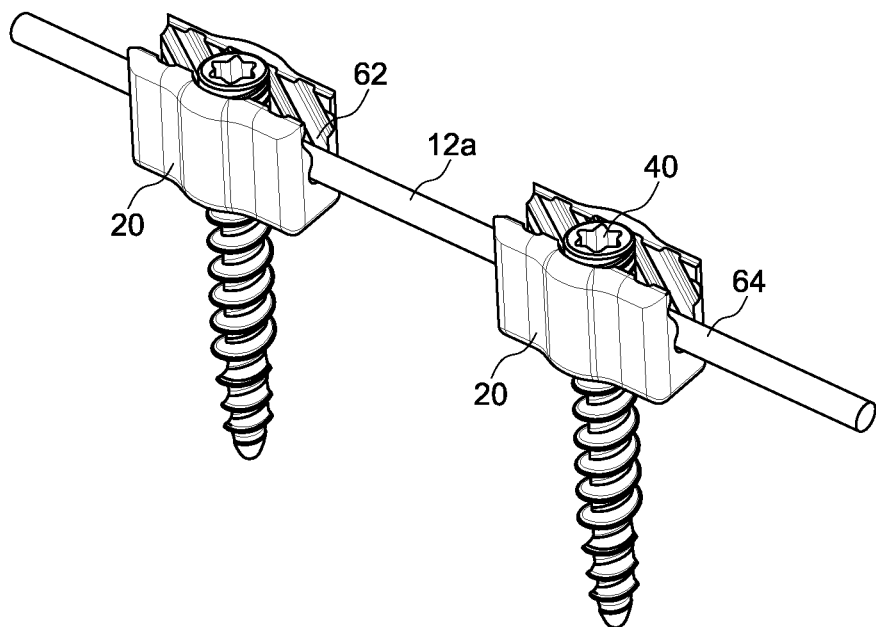
FIG. 17 is a top perspective view of a pair of tethering assemblies coupled together by a tether according to one embodiment of the present invention.
Figure 18:
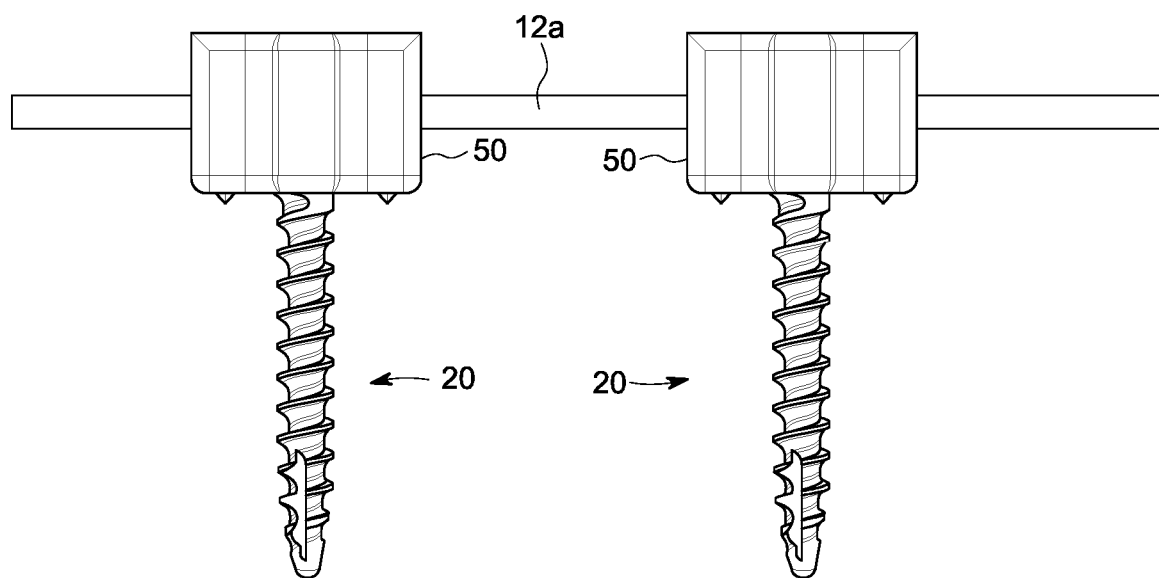
FIG. 18 is a side elevational view of the apparatus of FIG. 17.
Figure 19:
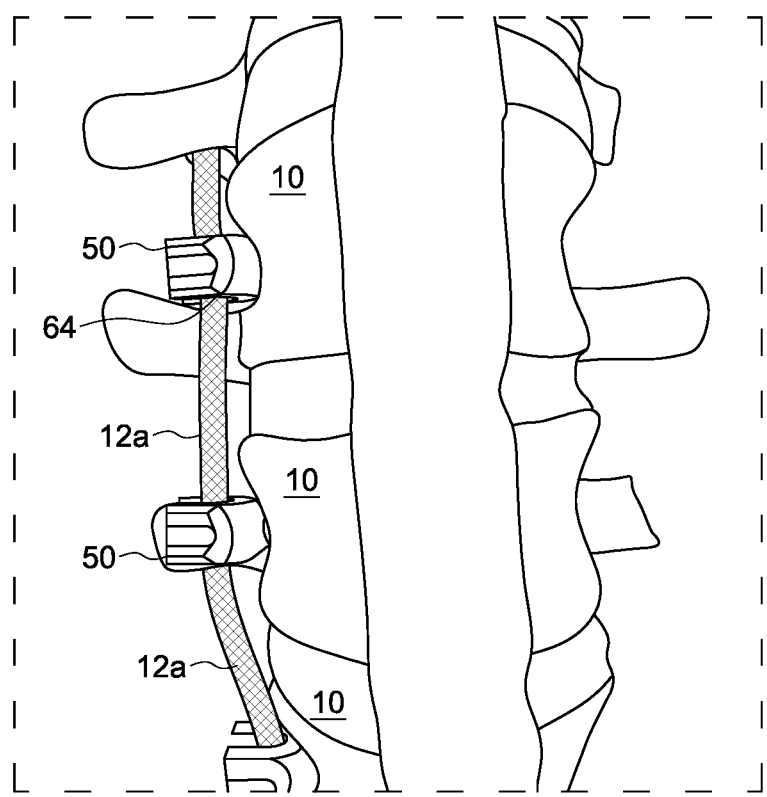
FIG. 19 is a photographic representation of the apparatus of FIG. 17 shown attached to a model of a spine.

FIGS. 17, 18, and 19 show a plurality of apparatus 20 coupled by a tether 12. The tether 12 includes an alternating pattern of compressed regions 12b (located within an apparatus 20) and largely uncompressed regions 12a located between adjacent apparatus 20. As best seen in FIG. 19, it is appreciated that the flexibility of the uncompressed regions 12a permit a coupling of bone surfaces along a nonlinear path, yet still permitting rotational flexibility of one bone member 10 of one vertebrae 10 coupled to another vertebrae 10.

Yet various other embodiments of the present invention contemplate apparatus and methods in which the number of grooves or teeth on the cleat can vary. The slope of the grooves or teeth can vary, and the angle between the sides can vary. Further, orientation of the cleat can be vertical or horizontal. If horizontally oriented, there may be a need for left and right side features to facilitate implantation. Still further embodiments utilize a proximal or distal orientation. When it is sideways (horizontal) the top is preferably smooth. The top can also include eyelets to close the pleura. The cord or tether may be flat or cylindrical (Rope), as examples. Various embodiments may or may not have a cap on top, and may rotate freely or be fixed relative to the vertebrae. Screws can be unicortical or bicortical.

FIGS. 20-30 depict various views of a tethering assembly 120 according to another embodiment of the present invention. Tethering assembly 120 preferably includes a cap that compresses the tether into a V-groove oriented such that the open side of the V is located laterally relative to the vertex, and generally perpendicular to the axis of the bone screw. This is different than some of the other embodiments shown herein in which the open side of the V is located above the vertex, in an orientation generally parallel to the axis of the bone screw. In still further embodiments the placement of the cap on a restraining member creates one or more additional V-grooves that assist in trapping, compressing, and frictionally restraining a flexible member at the exit of a pathway.

Figure 20:
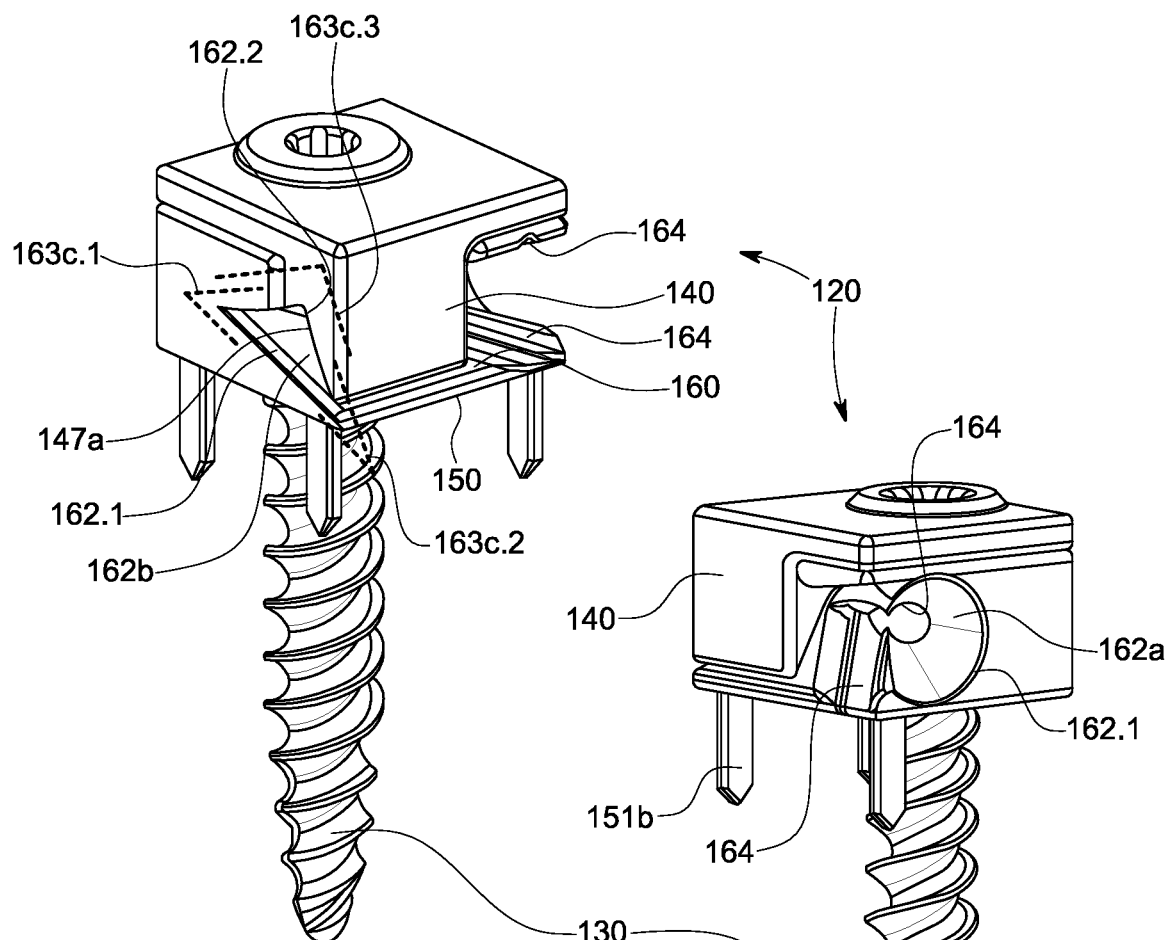
FIG. 20 is a top, side perspective CAD surface representation of a tethering assembly according to another embodiment of the present invention.
Figure 21:
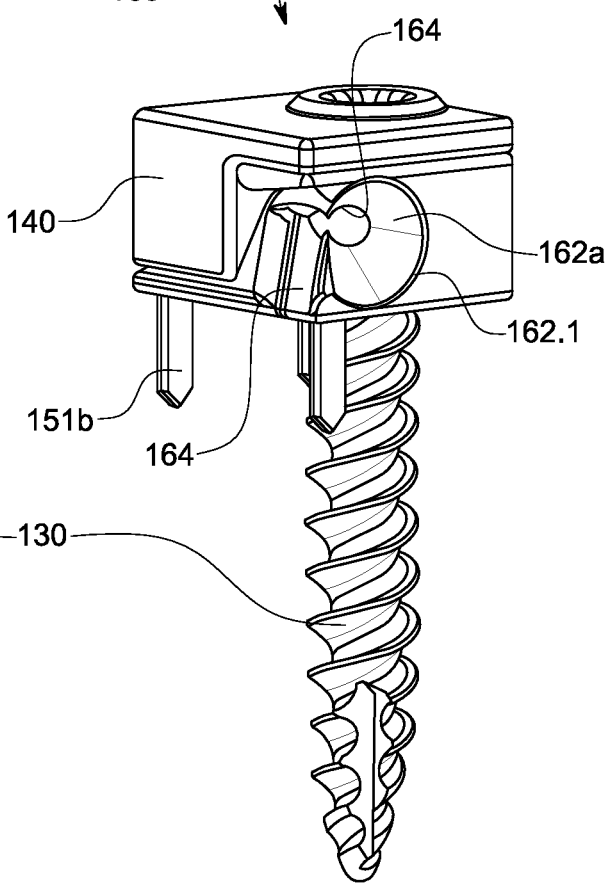
FIG. 21 is a perspective representation of the apparatus of FIG. 20, shown from a different side.
Figures 22, 23:
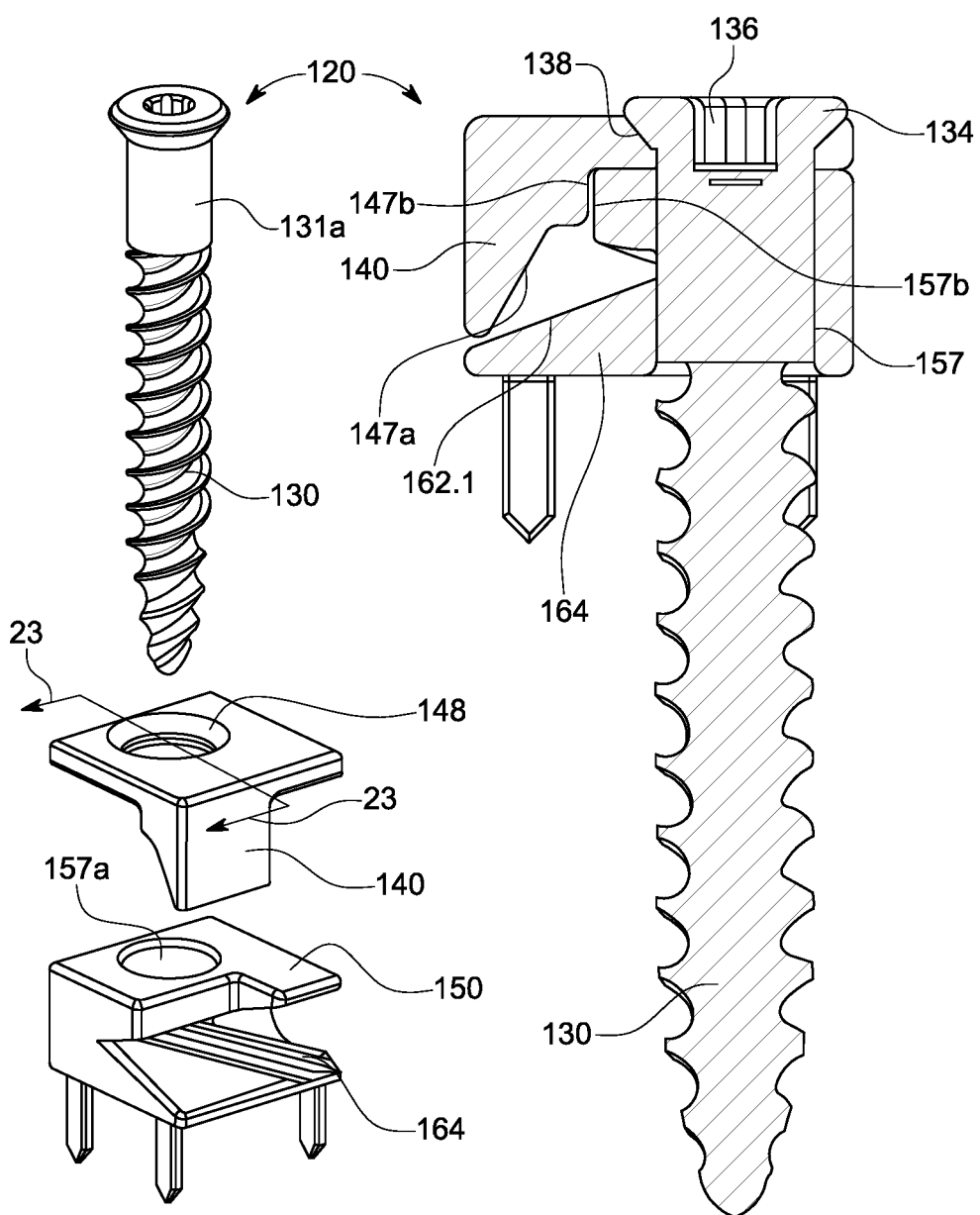
FIG. 22 is an exploded view of the apparatus of FIG. 20.
FIG. 23 is a side elevational cross sectional view, taken through the centerline of the fastener, of the apparatus of FIG. 22, non-exploded, as indicated by the line 23-23.
Figure 25:
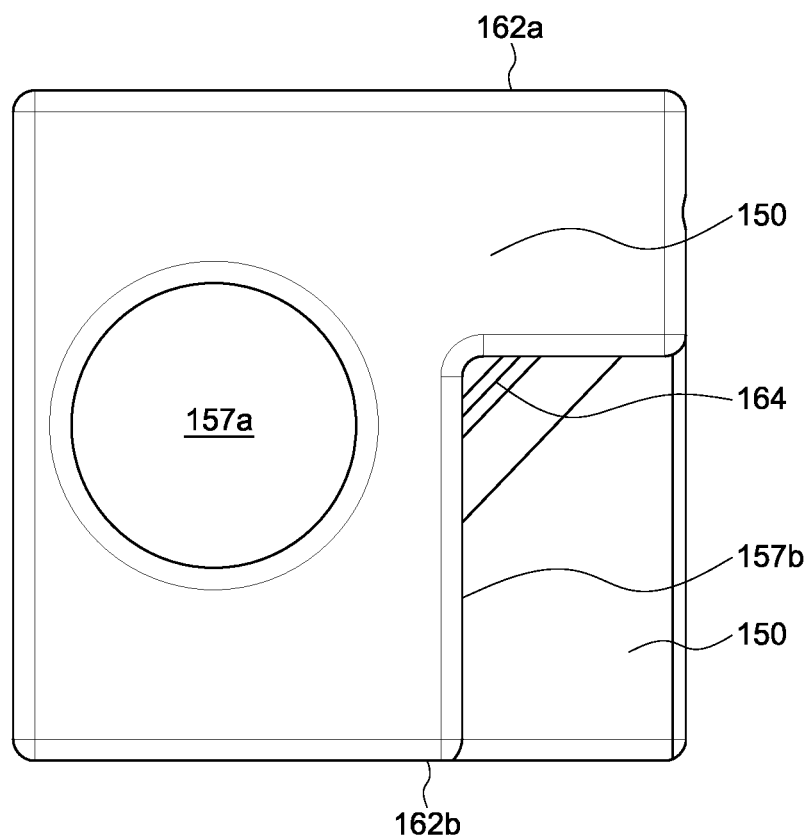
FIG. 25 is a top view of the apparatus of FIG. 24.

FIGS. 20-23 show various views of a tether assembly 120. Assembly 120 includes a tether restraining member 150, a cap 140, and a bone fastener 130. Referring to FIGS. 22 and 23, it can be seen that cap 140 includes an aperture 148, and restraining member 150 includes an aperture 157a, these apertures being brought into general alignment by fastener 130. The alignment of cap 140 and restraining member 150 is completed by the contact of abutment surfaces 157b and 147b. Referring briefly to FIGS. 25 and 26, it can be seen that the abutment surfaces for restraining member 150 are L-shaped and likewise the abutment surfaces of cap 140 are likewise L-shaped.

Figure 24:
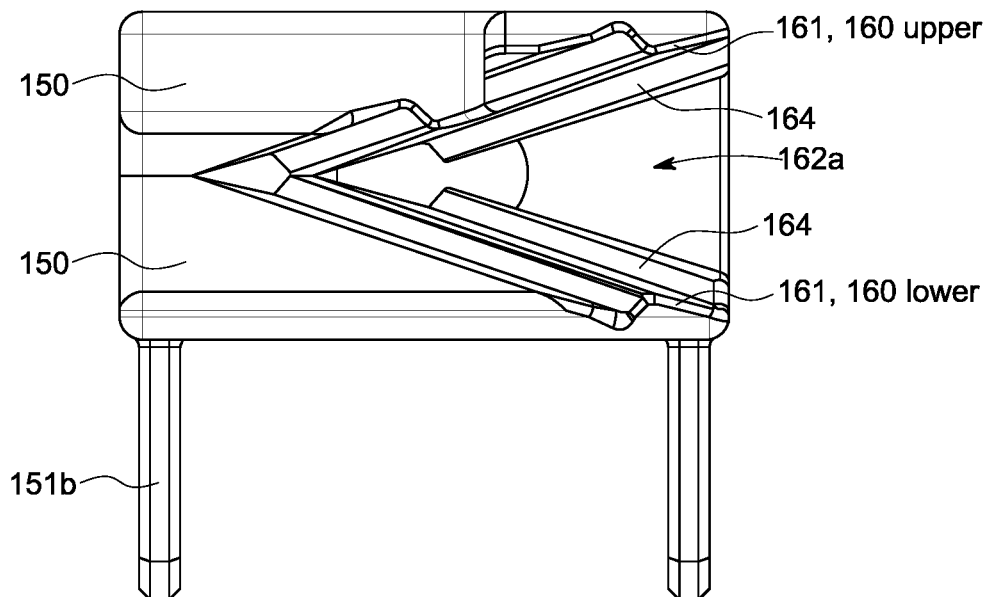
FIG. 24 is a side elevational view of a portion of the apparatus of FIG. 22.

Referring to FIGS. 20 and 21, it can be seen that the fitment of cap 140 to restraining member 150 forms a triangular-shaped exit 162b of a tether pathway having an entrance 162a. Referring to FIG. 24, it can be seen that entrance 162a includes a pair of lateral walls 160 each having inner surfaces 161 that include at least one flute or groove 164 (as also seen in FIG. 21). It can be seen that the grooves 164 are oriented to converge in a direction toward exit 162b. In some embodiments, these grooves 164 also converge in a direction toward the vertex of the upper and lower walls 160 (referring to FIGS. 24 and 20). These grooves function in a manner similar to that described previously for frictional restraint of the flexible connector.

Referring to FIGS. 24 and 28, it can be seen that the tether restraining member 150 includes at least one bone contacting member 151b, and preferably two or more such pointed projections. It is understood that attachment of tethering assembly 120 to a bone by fastener 130 results in these projections 151b penetrating the bone and securing the position of the tethering assembly on the bone surface. Although what has been shown and described is the attachment of a restraining member and cap by use of a bone fastener, it is understood that these components can further be coupled to a plate, such that the method used to compress the cap and the tether restraining member is not a fastener but some other device, with the plate being attached in any manner to the bone surface.

Referring to FIG. 20, it can be seen that the fitment and coupling of cap 140 on restraining member 150 in some embodiments forms a triangular exit 162b. As indicated by the three dashed Vs, the restraining member 150 includes a first channel having a direction of convergence as indicated by 163c.1. The vertex of this channel is part of a pathway for the flexible connector. This channel 162.1 is preferably V-shaped, with the open side of the V-shape (as best seen in FIG. 28) being laterally opposite of the vertex. The initial placement of tether within member 150 is therefore laterally from the open side of the V toward the vertex, again as indicated by direction of convergence 163c.1. This is different than some of the other tethering members shown herein, in which the V-shape is arranged generally vertically, or parallel to the axis of the fastener.

Referring briefly to FIG. 23, it can be seen that cap 140 includes a surface 147a that extends from the underside of the top of cap 140 downward toward the bottom leg of the first channel 162.1. In some embodiments, this surface 147a is angled as shown, so as to create a wedging or compression of the tether pathway as the cap is compressed by the head of fastener 130. However, in still other embodiments this surface 147a may extend in any orientation, including generally parallel to the axis of the fastener, or angled inward in a direction toward the axis, and also toward the vertex indicated by convergence direction 163c.1.

Referring again to FIG. 20, it can be seen that the alignment and fitment of cap 140 onto restraining member 150 forms a triangular-shaped tether exit. The wedging surface 147a cooperates with the bottom wall 160 of member 150 to create a bottom-facing V-shape and second channel 163c.2. Further, this wedging surface 147a further acts to compress the flexible member prior to its exit from the passageway toward the vertex created by the direction of convergence 163c.1. In addition, FIG. 20 shows that the wedging surface 147a of cap 140 further creates a V-shaped groove with the upper wall 160 of member 150 as indicated by third direction of convergence 163c.3. Referring to FIG. 28, it can be seen that any attempt to pull a flexible connector within member 150 will tend to move the flexible connector toward a region of minimum of width in first channel 162.1. Further, from FIGS. 28 and 21, it is noted that in some embodiments the entrance 162a, and at least a portion of the length of the flexible connector pathway has curved walls, and in some embodiments the entrance and walls have a circular shape.

Various aspects of different embodiments of the present invention are expressed in paragraphs X1, X2, X3, X4, X5, X6 and X7 as follows:

X1. One aspect of the present invention pertains to an apparatus for tethered connection between vertebrae. The apparatus preferably includes a portion of flexible tether having an uncompressed width. The apparatus preferably includes a tethering restraint member having a channel between opposing walls, the channel having an open top and a closed bottom, the open top extending from an entrance on a side of the tethering restraint member to an exit on a side of the tethering restraint member, the bottom including a region less wide than the uncompressed width of the tether, the region being adapted and configured for restraint of the tether within the channel.

X2. Another aspect of the present invention pertain to an apparatus for tethered connection between vertebrae. The apparatus preferably includes a tethering restraint member having a channel between opposing walls and extending from an entrance to an exit, each opposing wall including at least one groove that is not perpendicular to the channel and is not parallel to the channel, the opposing walls converging toward each other. The apparatus preferably includes means for attaching said tethering restraint member to a vertebra.

X3. Yet another aspect of the present invention pertains to an apparatus for tethered connection between vertebrae. The apparatus preferably includes a bone screw having a shaft with threads and an end with a concave driving feature. The apparatus preferably includes a portion of flexible tether having a width. The apparatus preferably includes a tethering restraint member having a longitudinal channel between opposing walls, the member defining a through aperture sized to accept therethrough the shaft, the tethering restraint member including a threaded portion within the channel to accept the threaded body, the channel including a region wherein the width of the channel is less than the uncompressed width of the tether, wherein the region is between the through aperture and the threaded portion.

X4. One aspect of the present invention pertains to an apparatus for tethered connection to a vertebra. The apparatus preferably includes a bone screw. The apparatus preferably includes a cap having a threaded body, a driving pocket on a proximal end, and a smooth surface on a distal end. The apparatus preferably includes a tethering restraint member having a V-shaped channel between opposing walls, the V-shaped channel including a region less wide than the uncompressed diameter of the tether, the member including threads to accept the threaded body with the smooth surface being proximate to the region.

X5. Another aspect of the present invention pertains to an apparatus for tethered connection to a vertebra. The apparatus preferably includes a bone screw having a shaft with threads and a head. The apparatus preferably includes a tethering restraint member having a longitudinally oriented V-shaped channel between opposing walls, the opposing surfaces of the walls including a plurality of grooves that are angled relative to the length or direction of the channel, such that movement of a tether within the channel in a first direction will move the tether toward the bottom of the channel, and toward increasing amounts of compression.

X6. Yet another aspect of the present invention preferably pertains to an apparatus for tethered connection to a vertebra. The apparatus preferably includes a bone screw having a shaft with threads and an end with a concave driving feature. The apparatus preferably includes a cap having a threaded body. The apparatus preferably includes a tethering restraint member having a longitudinal channel between opposing walls, the channel including a region wherein the width of the channel is less than the uncompressed diameter of the tether, said member defining a through aperture sized to accept therethrough the shaft, said member including a threaded portion to accept the threaded body, wherein the region is between the through aperture and the threaded portion.

X7. Still another aspect of the present invention pertains to an apparatus for tethered connection between bones. The apparatus preferably includes a cap having a wedging surface. The apparatus preferably includes a tethering restraint member having a first channel between first opposing converging walls, the first channel including a first region wherein the width of the channel between the first converging walls is a minimum; wherein alignment of the wedging surface relative to one of the converging walls creates a second channel between the wedging surface and the one wall.

Yet other embodiments pertain to any of the previous statements X1, X2, X3, X4, X5, X6 or X7 which are combined with one or more of the following other aspects. It is also understood that any of the aforementioned X paragraphs include listings of individual features that can be combined with individual features of other X paragraphs.

Wherein said member has a length between end, and the V-shaped groove extends along the length from one end to the other end.

Wherein the head of said bone screw is contained within said member when said screw is within the aperture.

Wherein the top of said cap is about flush with the top of said member when the cap is fully threaded into said member.

Wherein the tether is compressed within the channel between the bottom of the assembled cap and the bottom of the channel.

Wherein the region of the channel compressing the tether is between the head of said assembled screw and the bottom of said assembled cap.

Wherein said member has a longitudinal axis for the channel and the opposing ends of said member are open to permit passage therethrough of the tether.

Wherein said member includes an external bone contacting surface having at least one projection that extends toward the bone.

Wherein said screw includes an exterior shoulder, said body includes an interior shoulder surrounding the aperture, and the interior should is adapted and configured to prevent passage of the head through the aperture.

Wherein the through aperture extends generally perpendicularly to the longitudinal oriented V-shaped groove, and said member includes a bone contacting surface generally parallel to one of the sides of the V-groove.

Wherein the through aperture extends generally perpendicularly to the longitudinal oriented V-shaped groove, and said member includes a bone contacting surface generally opposite of the opening of the V-groove.

Wherein said member includes a bone contacting surface generally parallel to one of the sides of the V-groove.

Wherein said member includes a bone contacting surface generally opposite of the opening of the V-groove.

Which further comprises a cap having a threaded body and a driving pocket on a proximal end, and said member including threads within the surfaces of the walls to accept the threaded body.

Wherein at least one of the opposing walls includes a plurality of grooves that are angled and converge toward the bottom of the channel.

Which further comprises a means for attaching said tethering restraint member to a vertebra.

Wherein the at least one groove of each wall is angled toward the bottom of the channel in the same direction.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

Wherein the wedging surface and the one wall converge toward each other.

Wherein the region of the first channel includes a vertex between the converging walls.

Wherein the first opposing walls and the wedging surface form a triangular region adapted and configured to compress a tether therein.

Wherein the first channel includes a pathway for tether in a direction generally perpendicular to the axis of said bone screw.

Wherein the first channel includes a pathway for tether, each of the first opposing walls of the pathway including at least one groove that is not perpendicular to the channel and is not parallel to the channel.

Wherein the at least one groove on each of the first opposing walls converge in a direction toward the first region.

What is claimed is:

1. An apparatus for tethered connection between bones, comprising:
    a bone screw having a shaft with threads;
    a cap having a through aperture sized to accept therethrough the shaft, said cap including a wedging surface; and
    a tethering restraint member having a first channel between first opposing converging walls, said member defining a through aperture sized to accept therethrough the shaft, the first channel including a first region wherein the width of the channel between the first converging walls is a minimum;
    wherein placement of said screw through both the cap aperture and the member aperture and attachment of said screw to a bone aligns the wedging surface relative to one of the converging walls to create a second channel between the wedging surface and the one wall.

2. The apparatus of claim 1 wherein the wedging surface and the one wall converge toward each other.

3. The apparatus of claim 1 wherein the region of the first channel includes a vertex between the converging walls.

4. The apparatus of claim 1 wherein the first opposing walls and the wedging surface form a triangular region adapted and configured to compress a tether therein.

5. The apparatus of claim 1 wherein the first channel includes a pathway for a tether in a direction generally perpendicular to the axis of said bone screw.

6. The apparatus of claim 1 wherein the first channel includes a pathway for a tether, each of the first opposing walls of the pathway including at least one groove that is not perpendicular to the channel and is not parallel to the channel.

7. The apparatus of claim 1 wherein each of the first opposing walls includes at least one groove of a plurality of respective grooves, and wherein the respective grooves converge in a direction toward the first region.

* * * * *